(12) United States Patent
McGarrah et al.

(10) Patent No.: US 11,547,692 B2
(45) Date of Patent: *Jan. 10, 2023

(54) COMPLETE ANIMAL FOOD HAVING CANNABINOIDS IN TRACE CONCENTRATIONS TO AVOID TOXICITY

(71) Applicants: Steven M. McGarrah, Iverness, FL (US); Thomas A. Asquith, Cincinnati, OH (US)

(72) Inventors: Steven M. McGarrah, Iverness, FL (US); Thomas A. Asquith, Cincinnati, OH (US)

(73) Assignee: High Plains Nutrition, LLC, Inverness, FL (US)

( * ) Notice: Subject to any disclaimer, the term of this patent is extended or adjusted under 35 U.S.C. 154(b) by 210 days.

This patent is subject to a terminal disclaimer.

(21) Appl. No.: 17/094,673

(22) Filed: Nov. 10, 2020

(65) Prior Publication Data

US 2021/0106556 A1    Apr. 15, 2021

Related U.S. Application Data

(63) Continuation-in-part of application No. 15/923,695, filed on Mar. 16, 2018, now Pat. No. 10,849,852.

(60) Provisional application No. 62/473,369, filed on Mar. 18, 2017.

(51) Int. Cl.

| | |
|---|---|
| *A61K 31/352* | (2006.01) |
| *A61K 31/05* | (2006.01) |
| *A61K 9/00* | (2006.01) |
| *A61K 47/46* | (2006.01) |
| *A61K 47/44* | (2017.01) |
| *A23K 50/75* | (2016.01) |
| *A23K 20/20* | (2016.01) |
| *A23K 20/111* | (2016.01) |
| *A23K 20/121* | (2016.01) |
| *A23K 20/158* | (2016.01) |
| *A23K 50/40* | (2016.01) |
| *A23K 20/174* | (2016.01) |

(52) U.S. Cl.
CPC .......... *A61K 31/352* (2013.01); *A23K 20/111* (2016.05); *A23K 20/121* (2016.05); *A23K 20/158* (2016.05); *A23K 20/174* (2016.05); *A23K 20/20* (2016.05); *A23K 50/40* (2016.05); *A23K 50/75* (2016.05); *A61K 9/0056* (2013.01); *A61K 31/05* (2013.01); *A61K 47/44* (2013.01); *A61K 47/46* (2013.01)

(58) Field of Classification Search
CPC ........ A61K 31/352; A61K 31/05; A61K 9/00; A61K 47/46; A61K 47/44; A23K 50/75; A23K 20/20; A23K 20/111; A23K 20/121; A23K 20/158; A23K 50/40; A23K 20/174

See application file for complete search history.

(56) References Cited

PUBLICATIONS

DaPortaetal. Industrial Crops and Products 36(1):401-404 (2012) (Year: 2012).*
Treattibles CBD-Rich Oil Drops for Pets to True Farma (2018). (Year: 2018).*

* cited by examiner

*Primary Examiner* — Shirley V Gembeh
(74) *Attorney, Agent, or Firm* — Kevin H. Fortin, Esq.

(57) ABSTRACT

A nutritionally complete animal food including, vitamins, and minerals to sustain the animal's health and wellness. The one or more ingredients containing cannabinoids added to the nutritionally complete animal food at the time of manufacturing. These cannabinoids are selected from the group consisting of Cannabichromenic acid (CBCA), Cannabidiolic acid (CBDA), Cannabidivarinic acid (CBDVA), Cannabigerolic acid (CBGA), Cannabinolic acid (CBNA), Δ9-Tetrahydrocannabinolic acid (THCA), Tetrahydrocannabinolic acid (THCVA) and combinations thereof. The concentrations of each of the cannabinoids are each less than 100 parts per million (ppm) in the at least one ingredient. In an alternate embodiment, the one or more ingredients have cannabinoids include in an aggregate concentration of less than 100 parts per million (ppm).

20 Claims, 2 Drawing Sheets

COMPLETE ANIMAL FOOD HAVING CANNABINOIDS IN TRACE CONCENTRATIONS TO AVOID TOXICITY

This application is a continuation-in-part of U.S. patent application Ser. No. 15/923,695 filed Mar. 16, 2018 entitled Pet Food Including Cannabidiolic Acid which claims priority to provisional application No. 62/473,369 filed Mar. 18, 2017. This application also claims priority to provisional application No. 63/075,011 filed Sep. 5, 2020. The contents of each of these applications are incorporated herein in their entirety.

FIELD OF THE INVENTION

The present invention pertains to complete animal food products containing cannabinoids, and particularly to nutritionally complete feed rations including trace cannabinoids.

BACKGROUND OF THE INVENTION

Cannabinoids are substances capable of activating receptors in the endocannabinoid system of many animals including humans. Over a hundred different cannabinoids can be isolated from *cannabis* and these each exhibit varied effects. Many animals are sensitive to cannabinoids, and like many nutrients, a threshold amount to achieve bioactivity is desirable, but with many cannabinoids, high concentrations can be toxic.

Classical cannabinoids, as defined herein, are Tetrahydrocannabinol (THC), Tetrahydrocannabinolic acid (THC-A), Cannabidiol (CBD) and Cannabidiolic acid (CBD-A), although many other cannabinoids have been well documented and researched. The acid forms of theses classical cannabinoids predominate in the *Cannabis sativa* plant and other plants.

The seeds of the *Cannabis sativa* plant are rich in essential fatty acids, that are beneficial in animals including humans. These fatty acids are associated with reduction in inflammation and may address other health issues including obesity. Seeds of *Cannabis sativa*, namely industrial hemp, are often cold pressed to extract oils rich in essential fatty acids.

The flowers, leaves, seeds, stalks and stems of *Cannabis sativa* can be processed to extract oils containing various cannabinoids. The stems, leaves and seeds contain detectable amounts of certain cannabinoids. Cannabinoids and essential fatty acids, are known to have health benefits, including the reduction of inflammation.

Cannabidiol (CBD) is the most abundant classical cannabinoid in hemp oil (making up over 90% of the cannabinoid content). CBD has little affinity for CB1 or CB2 receptors, which are the main points of interaction for cannabinoids in the endocannabinoid system. CBD does act as an antagonist of cannabinoid agonists and thus has an indirect effect on the endocannabinoid system. CBD may temper the "high" caused by THC. CBD includes CBD-C1: Cannabidiol-C1, CBD-C4: Cannabidiol-C4, and CBD-A: Cannabidiolic Acid.

Cannabigerol is a precursor to other cannabinoids. Most CBG is transformed into other cannabinoids like CBD or THC by the plant or through other external processes. Natural CBG levels are very low in most *cannabis* plants. CBG has been isolated in its acid and non-acid forms.

Tetrahydrocannabinol is an abundant classical cannabinoid found in most medical and recreational marijuana strains. THC mimics the action of anandamide, a neurotransmitter naturally produced in the human body, and binds to CB1 receptors in the endocannabinoid system found mostly in the brain. However, in industrial hemp THC is a minor constituent and appears only in trace amounts under 3000 ppm (0.30%) by dry weight, as required by the regulations of many countries. Hemp oil derived from industrial hemp is non-psychoactive—due to its low THC content. THC has numerous forms and iso-forms including acid and non-acid forms. Examples include: THC-A-A: Delta-9-tetrahydrocannabinolic Acid A, THC-A-C 1: Delta-9-tetrahydrocannabiorcolic Acid, THC-A-C4: Delta-9-tetrahydrocannabinolic Acid C4, THC-A-B: Delta-9-tetrahydrocannabinolic Acid B, THC-C 1: Delta-9-tetrahydrocannabiorcol, THC-C4: Delta-9-tetrahydrocannabinol C4, iso-THC: iso-Tetrahydrocannabinol.

Cannabinol results from the degradation of THC. There is little Cannabidiol in the fresh plant, but decarboxylation often raises the amount of CBN in the plant. CBN is only mildly psychoactive and has a higher affinity for the CB2 receptor than the CB1 receptor, linking CBN to the body's immune system. In hemp oil, CBN is present in levels of 2000 ppm (0.2%) or lower. Other forms can include: CBN-C1: Cannabiorcol, CBN-C2: Cannabinol-C2, CBN-C4: Cannabinol-C4, CBND: Cannabinodiol.

Along with the primary cannabinoids and their variants, there are a number of minor cannabinoids whose benefits have not yet been thoroughly studied. Even in low quantities, these cannabinoids may interact with the endocannabinoid system and some of these minor cannabinoids include: CBC: Cannabichromene, CBL: Cannabicyclol, CBT: Cannabitriol, CBE: Cannabielsoin, CBR: Cannabiripsol, DCBF: Dehydrocannabifuran, CBF: Cannabifuran, CBCN: Cannabichromanon, and CBT: Cannabicitran. These minor cannabinoids, may be associated with the "Entourage Effect".

Like THC-A and CBD-A, there are other non-decarboxylated forms of cannabinoids present in *cannabis*. Once exposed to heat, light, or alkaline conditions, these cannabinoids lose a carboxyl group. The following acidic cannabinoids are typically found in *Cannabis*: CBCA: Cannabichromenic Acid, CBL-A: Cannabicyclolic Acid, CBEA-A: Cannabielsoic Acid A, CBEA-B: Cannabielsoic Acid B, CBNA: Cannabinolic Acid.

The "varin" type cannabinoids have the suffix -varin in their names. These differ in length from common cannabinoids, replacing the typical 5 carbon chain with a 3 carbon chain. These include: CBV: Cannabivarin, THCV: Tetrahydrocannabivarin, CBDV: Cannabidivarin, CBCV: Cannabichomevarin, CBGV: Cannabigerovarin, CBLV: Cannabicyclovarin, CBVD: Cannabinodivarin, CBTV: Cannabitriolvarin.

The following acidic forms of varin type cannabinoids are non-decarboxylated: CBGV-A: Cannabigerovarinic Acid, THCVA: Delta-9-tetrahydrocannabivarinic Acid, CBDVA: Cannabidivarinic Acid, CBCVA: Cannabichromevarinic Acid.

Various ether form cannabinoids have been discovered. These include: CBG-AM: Cannabigerolic Acid Monomethyl Ether, CBGM: Cannabigerol Monomethyl Ether, CBDM: Cannabidiol Monomethyl Ether, CBNM: Cannabinol Methyl Ether, CBTVE: Ethoxy-cannabitriolvarin. While trace quantities of these ether form cannabinoids found in hemp oil, some believe that these ether form cannabinoids are partially responsible for the entourage effect and may influence bio-activity of the other cannabinoids.

The endocannabinoid system includes receptors that bind cannabinoids. CB1 and CB2 are well-documented receptors for cannabinoids. The CB1 receptors are present in the brain.

The CB2 receptors are not fully mapped but are believed to be concentrated in the immune and hematopoietic systems. Cannabinoids can cause biological effects by binding to these and to additional receptors.

The endocannabinoid system also includes enzymes that make or degrade endocannabinoids from arachidonate-based lipids. Agonistic activity by endocannabinoids on the CB1 and CB2 receptors yields many well-documented health benefits.

Phytocannabinoids are plant-derived cannabinoids that modulate the endocannabinoid system. Although phytocannabinoids are found in many plants, the highest, known concentrations are found in *Cannabis sativa*. Common names for the well-known varieties in the *cannabis* family are hemp and marijuana. The most abundant acidic classical phytocannabinoids typically found in freshly harvested *Cannabis sativa* are Tetrahydrocannabinolic acid (THC-A) and Cannabidiolic acid (CBD-A), although others also exist.

The term phytocannabinoids should be broadly understood to refer to any plant derived compound that affects the cannabinoid regulatory system and found in *Cannabis sativa* or other plants. In addition to the classical cannabinoids, phytocannabinoids also include some terpenes (e.g. caryophyllene), alkylamides (e.g. isobutylamide) and polyynes (e.g. falcarinol).

According to some research, CBD has minimal affinity for CB1 or CB2 receptors, and may act as an indirect antagonist of cannabinoid agonists.

CBD may also be a 5-HT1a and 5-HT2a receptor agonist. Interactions between receptors and cannabinoids are continually being discovered. As the science evolves there is mounting evidence that the ability of being able to select and optimally deliver a preferred cannabinoid mixture is desirable. Recent research provides surprisingly beneficial health effects achieved through the utilization of micro doses of cannabinoids on a regular basis for long continuous periods, i.e. several months.

The term "entourage effect" is applicable to cannabinoids because combinations of cannabinoids have been found to be more bioactive than individual cannabinoids.

While the health benefits of consumption of phytocannabinoids are well documented, there are drawbacks of smoking *cannabis*. Many medical marijuana patients prefer edibles over smoked marijuana because smoking is not typically associated with improved health and may aggravate certain health conditions. Unfortunately, intense processing of edibles is especially common. In particular, many edibles that include cannabinoids are cooked, pasteurized, sterilized, baked, heat dried, or extruded. These processes will typically convert a significant portion of the classical cannabinoids from their acidic forms to into the non-acidic decarboxylated forms.

Edible *cannabis* infused products include *cannabis* extracts as an ingredient. However, the processes used to extract the cannabinoids may also convert a high percentage of the naturally occurring acid forms of the primary phytocannabinoids into non-acid forms through the process of decarboxylation. Decarboxylation causes THC-A, for example, to convert to THC. THC is associated with increased psychoactive effects when compared to its precursor THC-A. While THC may occur naturally, decarboxylation of cannabinoids, including THC-A and CBD-A can occur by various mechanisms. While there are many health benefits to both acid and non-acid forms of these molecules, acidic cannabinoids have different pharmacologies and therapeutic effects than the decarboxylated forms.

According to some researchers, there are limits to the rate that fully decarboxylated THC that can be absorbed by the body. Since THC-A and CBD-A have different pharmacologies than their decarboxylated counterparts, it's preferable to control the amounts of acidic and non-acidic cannabinoids in edible products.

Many cannabinoids, including terpenes, are volatile or unstable in the presence of heat or intense processing. Current ways of processing and delivering cannabinoids through food products may volatilize or change the molecular structures of some cannabinoids. Accordingly, an intensely processed food with cannabinoids in an oil may have different therapeutic outcomes than a less processed food.

Typically, products derived from hemp that contain less than 3000 ppm (0.30% dry weight) of tetrahydrocannabinoids are exempt from the legal definition of marijuana in the United States, for example.

U.S. Pat. No. 7,399,872 to Mechoulam et al. describes a way of converting CBD into THC under lab conditions using a specialized reaction mixture an organic solvent and $NaHCO_3$. There is anecdotal evidence that similar reactions may occur in the gastric juice of humans. Gastric juice, or gastric acid, contains hydrochloric acid (HCl), potassium chloride (KCl) and sodium chloride (NACl) along with numerous enzymes that are activated by these acids. Molecules including CBD may convert into THC in the presence of gastric acid.

While the amount of CBD that may convert to THC under gastric conditions may be small, some consumers may wish to consume products that are less capable of producing THC.

Patients may also prefer that their medical marijuana be optimized for potency through the entourage effect by the full inclusion of the naturally occurring array of cannabinoids. Further, cannabinoids in the acid forms are preferred because the higher therapeutic doses are possible without negative side effects such as psycho activity. A patient can typically tolerate higher and more effective doses of cannabinoids without the psychoactive side effects associated with the decarboxylated (non-acid) forms.

What is desired is: 1) food manufacturing processes that yield functional foods having micro-doses of cannabinoids and that enable an entourage effect in vivo, 2) functional foods that predominately include acidic forms of cannabinoids. 3) food manufacturing processes that yield food products for humans or animals, where the food products have a more controlled composition of cannabinoids, 4) food products that include predominately the acid-form of at least one desired cannabinoid.

SUMMARY OF THE INVENTION

The present invention includes a nutritionally complete animal food, including an extruded food substrate, which includes essential nutrients to provide an animal dietary homeostasis, the essential nutrients includes a ratio of omega-6 fatty acids and omega-3 fatty acids of between 3:1 and 5:1, for example.

The nutritionally complete animal food includes dietary supplements including phosphorous, potassium, magnesium, sulfur, calcium, iron, and zinc.

Cannabinoids are also included in a concentration of less than 100 ppm for any particular cannabinoid. The cannabinoids can be included as hemp cake or hemp oil in the extruded food substrate.

In one embodiment, the food substrate has a high omega-3 content which cooperates with the cannabinoid content to reduce inflammation.

Preferably the ratio of cannabidiolic acid and any other cannabinoid is at least 1:3, assuring a sufficient concentration of cannabidiolic acid to achieve bio-efficacy to reduce inflammation, manage pain, and to balance the animal endocannabinoid system without undue risk of toxicity.

In a preferred embodiment of the invention, the nutritionally complete animal food includes vitamins, and minerals to sustain the animal's health and wellness. The animal can be equine, canine, bovine, feline, or avian in various embodiments. The nutritionally complete animal food is adapted accordingly.

The animal feed includes one or more ingredients containing cannabinoids added to the nutritionally complete animal food at the time of manufacturing. The cannabinoids are selected from the group consisting of Cannabichromenic acid (CBCA), Cannabidiolic acid (CBDA), Cannabidivarinic acid (CBDVA), Cannabigerolic acid (CBGA), Cannabinolic acid (CBNA), $\Delta$9-Tetrahydrocannabinolic acid (THCA), Tetrahydrocannabinolic acid (THCVA) and combinations thereof.

The individual concentrations of each of the cannabinoids are each less than 100 parts per million (ppm) in the at least one ingredient. In a variation of the invention, the combined concentrations of these individual cannabinoids are all less than 100 parts per million (ppm) in the at least one ingredient. One reason for the limitation of cannabinoids to trace concentrations is to minimize the possibility of toxicity to the animal over time when the sole feed ration contains cannabinoids. Further, each ingredient is limited to 100 parts per million cannabinoid concentrations for each cannabinoid, or for combined cannabinoids, to eliminate the possibility of harm to an animal due to toxicity over time, where the ingredient usage varies from the recommended usage.

For example the food is formulated to limit the daily intake of any individual cannabinoid in the group to a maximum of 1.5 parts per million (ppm) per kilogram (kg) of body weight per 24 hr. day (1.5 ppm/kg BW/day) under normal and repeated feeding conditions to sustain the animal's health and wellness.

Edible oils are ingredients included in many, if not most, packaged foods. Common edible oils include olive oil, rapeseed oil, sunflower oil, corn oil, tallow, lard, chicken fat, and soybean oil. These can be supplemented with cannabinoids because cannabinoids exhibit a high degree of solubility in these edible oils. Since edible oils are also used in many food products, edible oils can be used as a carrier to add cannabinoids to edible products without significantly changing a recipe or without adversely influencing flavor. Some edible oils (i.e. hemp oil) naturally contain phytocannabinoids.

One drawback of traditional food processing methods is that heat is typically applied during the manufacture of packaged food products. Cannabinoids can react during production of food products in the presence of heat which changes the composition of the cannabinoids. The present invention includes products and methods for adding combinations of edible oils and cannabinoids that minimize changes in the composition of cannabinoids in certain edible products including extruded food products, baked food products, nut butters, spreads, pourable dressings, pelleted feeds, cold sausages and many other processed foods.

In one embodiment of the invention an extruded food product includes a food substrate manufactured by a hot extrusion process and having a cannabinoid mixture. The hot extrusion process is typically performed at above 80° C.

In another embodiment of the invention, a pet food product manufactured by extrusion or another method includes a food substrate having a blended combination of edible oils including a cannabinoid mixture. The first oil is hemp oil having cannabidiolic acid (CBD-A), and tetrahydrocannabinol (THC). The THC has a concentration of less than 100 ppm in the hemp oil. The THC and the CBD-A comprise primary functional components of the cannabinoid mixture.

Preferably, the hemp oil is cold pressed having a ratio of CBD-A to THC that is at least 1:3. It can be appreciated that an alternate embodiment has the same ratio replacing the CBD-A with CBD. In a further embodiment, the ratio of the combination of CBD and CBD-A to THC is at least 1:3

It can be appreciated that an alternate embodiment has the ratio of CBD-A to THC-A that is at least 1:3. In a further embodiment, the ratio of at least 1:3 comprises the combination of CBD and CBD-A, to the combination of THC and THC-A.

The pet food product includes a second oil being blended with the hemp oil to inhibit oxidation of the CBD-A and THC-A, non-acid forms of these molecules, other cannabinoids, and combinations thereof. The blended combination of hemp oil and the second oil are applied to the food substrate and do not exceed 10% of the pet food product by weight.

The cannabinoid mixture particularly includes primarily non-decarboxylated cannabinoids selected from the group consisting of A-9-tetrahydrocannibolic acid (THC-A), A-9-tetrahydrocannibolic acid (THC-B), A-9-tetrahydrocannibolic acid-$C_4$ (THC-A-$C_4$), A-9-tetrahydrocannibivarinic acid, A-9-tetrahydrocannibiorcolic acid (THC-A-C1), A-8-tetrahydrocannibolic acid ($A^8$-THC-A), cannabicyclolic acid (CBL-A), cannabidiolic acid (CBD-A), cannabigerolic acid (DBG-A), cannabigerovarinic acid (CBGV-A), cannabichromenic acid (CBCA), cannabichromevarinic acid (CBCVA), cannabidivarinic acid (CBDVA), cannabielsoic acid A (CBEA-A), cannabielsoic acid B (CBEA-B), cannabigerolic acid A monomethyl ether (CBG-AM-$0_5$ A) and cannabinolic acid (CBNA), and combinations thereof.

The food substrate may also include decarboxylated cannabinoids selected from the group consisting of CBD, THC and combinations thereof. This can be due to natural decarboxylation over time, or due to the natural occurrence of the decarboxylated forms in the live plant material, or other factors that are not controlled. Preferably the cannabinoids are primarily in the non-decarboxylated forms.

In one embodiment of the invention, the ratio by weight of Cannabidiolic Acid to cannabidiol is greater than 1:1. Preferably the ratio is greater than 3:1. In one embodiment the ratio is greater than 9:1. In another embodiment of the invention, the ratio by weight of Tetrahydrocannabinolic acid (THC-A) to Tetrahydrocannabinol (THC) is greater than 1:1. In one embodiment, the ratio is greater than 9:1.

The cannabinoid mixture further may include added phytocannabinoids, such as terpenes, alkylamides and terpenes, carotenoid, phenolic compounds and phytosterols to quench oxygen and to scavenge free radicals thereby reducing oxidation of Cannabidiolic Acid, and other classical cannabinoids and to optimize entourage effects.

The cannabinoid mixture is added to the food substrate after the food substrate is extruded, and after it cools to below 80° C. This relatively low temperature minimizes the degradation or volatilization of many of these other phytocannabinoids. Table 1 shows tested ratios of CBD-A:CBD, CBD-A:THC and CBD:THC in various hemp oil samples.

TABLE 1

| CBD-A:CBD | CBD-A:THC | CBD:THC |
|---|---|---|
| 3.69 | 1.88 | 0.510051 |
| 1.99 | 2.01 | 1.010101 |
| 2.51 | 2.69 | 1.070107 |
| 6.74 | 2.36 | 0.350035 |
| 3.00 | 2.97 | 0.990099 |

According to Table 1, the ratio of CBD-A:CBD is between approximately 2:1 and 7:1. The ratio varies because many hemp oils have varying ratios.

The ratio of CBD-A:THC varies between approximately 2:1 and 3:1. The ratio of CBD:THC varies between approximately 1:2 and 1:1 in the examples provided in Table 1. It can be appreciated that these ratios are examples only and the ratios can vary or be modified as desired.

In an alternative embodiment, the cannabinoid mixture is mixed with edible oil and added to the food substrate prior to a cold extrusion process. Preferably, the edible oil includes significant concentrations of omega-3 fatty acids. Preferably, the edible oil can include a portion of hemp oil, flax seed oil, or other oil rich in omega-3 fatty acids.

The food product in one embodiment is pasta, a breakfast cereal product, a snack bar, or a pet food formed into kibbles. It can be appreciated that the process and product described herein can be formed into any of a variety of food products.

In one embodiment of the invention, the cannabinoid mixture includes cannabinoids selected from the group consisting of, cannabigerol, cannabichromene, cannabicyclol, cannabivarian, tetrahydrocannabivarin, cannabidivarin, cannabichromevarin, cannabigerovarin, cannabigerol monomethyl ether, and combinations thereof. These cannabinoids may be in their acid forms, non-acid forms, or combinations thereof. These phytocannabinoids can be derived from *Cannabis sativa*, other plants, or synthetically derived.

In another embodiment, the extruded food product is manufactured by the hot extrusion process at temperatures greater than 80° C. The extruded food product is cooled to 80° C. or below, and the cannabinoid mixture is added after the step of cooling to inhibit decarboxylation of any component of the cannabinoid mixture. It can be appreciated that there still may be an inconsequential degree of decarboxylation but that an optimal ratio can be maintained.

While the cannabinoids can be derived from numerous sources, the ideal cannabinoid mixture is derived from a whole plant extracts of *Cannabis sativa*. More preferably, the cannabinoid mixture is derived solely from hemp having a THC concentration of less than 3000 ppm (0.3% by dry weight) as measured on a dry weight basis.

The edible oil including the cannabinoid mixture coats the food substrate through mixing. In another embodiment, the cannabinoid mixture coats the food substrate by spraying. In another embodiment, the cannabinoid mixture coats the food substrate by dipping or bathing.

The edible oil including the cannabinoid mixture is processed to inhibit microbial contamination. This process is selected from the group consisting of: irradiation, filtration, pressure treatment, bactericide addition, antibiotic addition, or combinations thereof, in a way that does not significantly decarboxylate the acid forms of cannabinoids. The edible oil processing maintains the desired ratio by weight of any one non-decarboxylated phytocannabinoid to its decarboxylated phytocannabinoid form of greater than 9:1 and possibly up to the ratio naturally found in freshly harvested natural *cannabis* biomass, or any ratio greater than 9:1. To inhibit decarboxylation of the cannabinoids the edible oil including the cannabinoid mixture does not exceed a temperature of 80° C. at any time during processing according to one embodiment of the invention.

Ideally the cannabinoid mixture further includes terpenes and alkylamides to enable a desired entourage effect. It may optionally further include polyynes. It can be appreciated that the cannabinoid mixture can be pre-determined and optimized to achieve the desired concentrations of cannabinoids. Preferably, the terpenes and alkylamides are derived from *Cannabis sativa*. It can be appreciated that where a desired cannabinoid mix is determined, various terpenes, alkylamides and polyynes can be added to fortify the cannabinoid mixture. It can be further appreciated that other phytocannabinoids can be added to fortify the cannabinoid mixture. Lastly it can be appreciated that cannabinoids derived from any source, natural or synthetic, can be added to fortify the mixture. These can be derived from any source, including plants such as *Cannabis sativa*.

The present invention encompasses dry packaged food products, including baked goods, snacks, breads, muffins, cakes and cookies. Many of these are cooked or otherwise dehydrated to a moisture content of less than 15% by weight to inhibit spoilage, maximize shelf life, and conform to modern taste preferences. The dry food substrate having a cannabinoid mixture including, non-decarboxylated phytocannabinoids including those selected from the group consisting of A-9-tetrahydrocannibolic acid (THC-A), A-9-tetrahydrocannibolic acid (THC-B), A-9-tetrahydrocannibolic acid-$C_4$ (THC-A-$C_4$), A-9-tetrahydrocannibivarinic acid, A-9-tetrahydrocannibiorcolic acid (THC-A-$C_1$), A-8-tetrahydrocannibolic acid ($A^8$-THC-A), cannabicyclolic acid (CBL-A), cannabidiolic acid (CBD-A), cannabigerolic acid (DBG-A), cannabigerovarinic acid (CBGV-A), cannabichromenic acid (CBCA), cannabichromevarinic acid (CBCVA), cannabidivarinic acid (CBDVA), cannabielsoic acid A (CBEA-A), cannabielsoic acid B (CBEA-B), cannabigerolic acid, A monomethyl ether (CBG-AM-$0_5$ A) and cannabinolic acid (CBNA), and combinations thereof.

The dry food substrate includes decarboxylated phytocannabinoids including those selected from the group consisting of CBD, THC, and combinations thereof. In one embodiment, the dry packaged food products include only non-decarboxylated cannabinoids.

Optimally, the ratio by weight of non-decarboxylated phytocannabinoids to decarboxylated phytocannabinoids is greater than 1:1. Preferably the ratio is greater than 3:1. In another embodiment there are no decarboxylated cannabinoids.

While some embodiments of the present invention utilize CBD-A and TCH-A, it can be appreciated that a variety of acidic cannabinoids can be utilized in accordance with the present invention. Although particular genetics, and growing conditions, can be adapted to produce any of a variety of cannabinoid profiles, it is expected that certain cannabinoids and other components can be extracted and re-combined in optimal concentrations to achieve the goals of the present invention.

The dry packaged food product is baked, or otherwise cooked. The cannabinoid mixture is dissolved into an edible oil. This edible oil may be sprayed or otherwise applied to the food substrate. In one embodiment, the edible oil impregnates the food substrate. In another embodiment, the cannabinoid mixture dissolves into, or is mixed with, the edible oil and at least partially coats the food substrate.

Preferably the edible oil is pre-processed to inhibit microbial contamination by a process selected from the group consisting of: irradiation, filtering, pressure treatment, or combinations thereof. More preferably, the cannabinoid mixture and the edible oil are processed together in a way that does not significantly modify the ratio of non-decarboxylated to decarboxylated classical cannabinoids.

In a variation of this embodiment, the cannabinoid mixture and edible oil are processed to inhibit microbial contamination In an embodiment of the invention, the edible oil including the cannabinoid mixture does not exceed a temperature of above 80° C. during processing to inhibit significant modification of the cannabinoids and to maintain the ratio.

A variation of the invention includes an edible oil product. This can be distributed to food manufacturers for use in packaged food products. The edible oil product includes a cannabinoid mixture. The cannabinoid mixture includes predominately acidic cannabinoids.

The edible oil product is processed to inhibit microbial and pathogenic contamination and to assure food safety. This process can be applied to the combined edible oil and cannabinoid mixture in a way that does not significantly change the amount of acidic—cannabinoids in the edible oil. In another embodiment this process can be applied to the edible oil and the cannabinoid mixture separately, prior to combination of the edible oil and the cannabinoid mixture. In this way, the edible oil can be processed in conventional ways, and the cannabinoid mixture can be processed in a way that optimizes the stability of the acidic cannabinoids, and other cannabinoids including terpenes.

The edible oil is preferably processed by a method selected from the group consisting of: irradiation, filtering, pressurization, or combinations thereof. This process inhibits microbial and pathogenic contamination and thereby preserves the edible oil, improving its shelf life and stability.

Various edible oils are available for utilization with the present invention. In one embodiment the edible oil is included in a nut butter. Preferably, this is simply mixed with the edible oil containing the cannabinoid mixture. The product is a cannabinoid infused nut butter that is shelf stable. In this embodiment, the nut butter is pre-processed to eliminate microbial and pathogenic contamination.

In another embodiment, the mixture of nut butter and the edible oil including the cannabinoid mixture is preserved by a process selected from the group consisting of: irradiation, filtering, pressurization, or combinations thereof.

The invention includes a liquid food product such as a condiment spread that includes other edible oil mixed with hemp oil having cannabinoids.

The cannabinoid mixture includes non-decarboxylated phytocannabinoids selected from the group consisting of CBD-A, THC-A, and combinations thereof. The food substrate including decarboxylated phytocannabinoids selected from the group consisting of CBD, THC, and combinations thereof. In another embodiment, the non-decarboxylated phytocannabinoids are chosen from those described in this patent application, and combinations thereof.

The ratio by weight of non-decarboxylated (acid form) phytocannabinoids to decarboxylated (non-acid form) phytocannabinoids is greater than 1:1.

The cannabinoid mixture is dissolved into another edible oil, which is mixed with the food substrate at a temperature of less than 80° C. during manufacture to inhibit decarboxylation of the cannabinoids in the cannabinoid mixture. Preferably, the cannabinoid mixture contains predominately acidic cannabinoids and contains minimal amounts of THC, Preferably, the cannabinoid mixture is directly extracted from the *Cannabis sativa* plant and has a cannabinoid mix that is reflective of the naturally occurring cannabinoid mix found in the plant. It can be appreciated that the cannabinoid mixture can contain supplemental cannabinoids that are added. The cannabinoid mixture can be derived from isolated and/or synthesized cannabinoids that are separated, then re-mixed in a formulation according to a pre-determined combination of cannabinoids to achieve desirable therapeutic results and improved product consistency.

In one embodiment of the invention, a pet food product includes a baked or extruded food substrate. The food product further includes hemp oil having cannabidiolic acid (CBD-A) concentration of between 15-55 ppm, and tetrahydrocannabinol (THC). The ratio of CBD-A to THC is at least 1.88:1 in the hemp oil. The food product includes a second oil blended with the hemp oil to inhibit oxidation of the CBD-A. The blended combination of hemp oil and the second oil are applied to the food substrate and do not exceed 10% of the food product by weight.

The invention alternatively includes a pet food product including a baked or extruded food substrate. The food product further includes hemp oil having hemp oil having a cannabidiol (CBD) concentration of between 15-50 ppm, and tetrahydrocannabinol (THC) where the ratio of CBD to THC is at least 0.35:1; in the hemp oil. The food product includes a second oil blended with the hemp oil to inhibit oxidation of the CBD-A. The blended combination of hemp oil and the second oil are applied to the food substrate and do not exceed 10% of the food product by weight.

DETAILED DESCRIPTION

Figure 1:
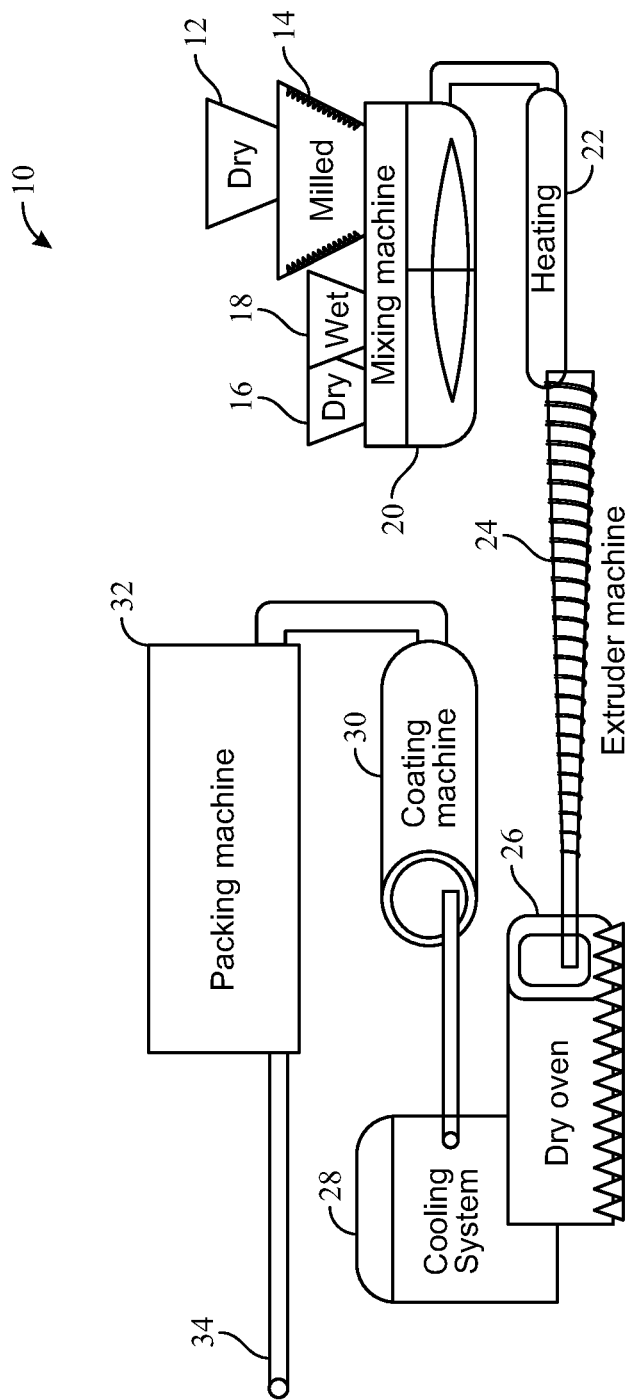
FIG. 1 is an extrusion system in accordance with the present invention.

FIG. 1 is a system in accordance with the present invention, generally designated with the reference numeral 10. The system 10 includes a series of hoppers that feed the mixing machine. There is a primary dry hopper 12 and a primary milled hopper 14 that directly feed primary ingredients into the mixing machine 20. Temperature of the mixing machine can be controlled to deliver desired processing control. The system 10 could further include a secondary dry hopper 16. Liquid ingredients can be pre-mixed in a tank 18 and then pumped into the mixer. Alternatively, liquids are directly pumped into the mixer as separate ingredients. Accordingly, any of a variety of mixed ingredients can be selectively and automatically delivered to the mixing machine 20. The mixing machine 20 produces a food substrate that is further modified by the system and methods of the present invention. In one embodiment, the mixer including a heater and the step of heating 22 occurs simultaneously with the mixer 20. In another embodiment, mixing and heating are accomplished sequentially.

The mixing machine 20 guides the food substrate to an extruder machine 24. The extruder machine 24 includes an auger to compress and move the food substrate through the extruder to yield an extruded food substrate. The extruded food substrate is then moved to a dry oven 26 to remove moisture from the extruded food substrate. Once the moisture is removed the food substrate is conveyed to a cooling system 28 which reduces the temperature of the food substrate to below 80° C. Optionally, the dryer oven and cooling system occur within the same machine. The cooled food substrate is conveyed to a coating machine 30, which is adapted for applying an edible oil and flavors to the cooled food substrate. The coating machine 30 is capable of spraying an edible oil onto a food substrate and thereby coating the food substrate with the edible oil. Ideally the spraying process is optimized to enable absorption of the edible oil into the food substrate. The edible oil includes a cannabinoid mixture.

In one embodiment of the invention the coating machine 30 is equipped with sprayers that uniformly spray the extruded food substrate with the edible oil. In another embodiment, the coating machine 30 includes a fluid bed processor for uniformly coating the extruded food substrate with the edible oil. It can be appreciated that various flavor components can be further sprayed or combined for spraying in accordance with the present invention.

The food substrate moves from the coating machine 30 to a packing machine 32. The packing machine divides and packages the food substrate into desired portions for fulfillment and delivery. Accordingly, an extruded food product 34 is produced.

In one embodiment the extruded food product 34 is a pet food such as a dried kibble. In another embodiment the extruded food product 34 is pasta. In yet another embodiment the extruded product 34 is a snack bar. In another embodiment the extruded food product 34 is pasta. In yet another embodiment the extruded product 34 is a cold meat or sausage product.

Importantly, notwithstanding processing of the food substrate, the edible oil having the cannabinoid mixture maintains desired ratios of the acidic cannabinoids or combinations thereof, when compared to the non-acid (decarboxylated forms). Preferably, these ratios are unchanged while the food substrate is infused with the edible oil because the food substrate is maintained at a temperature of less than 80° C.

Figure 2:
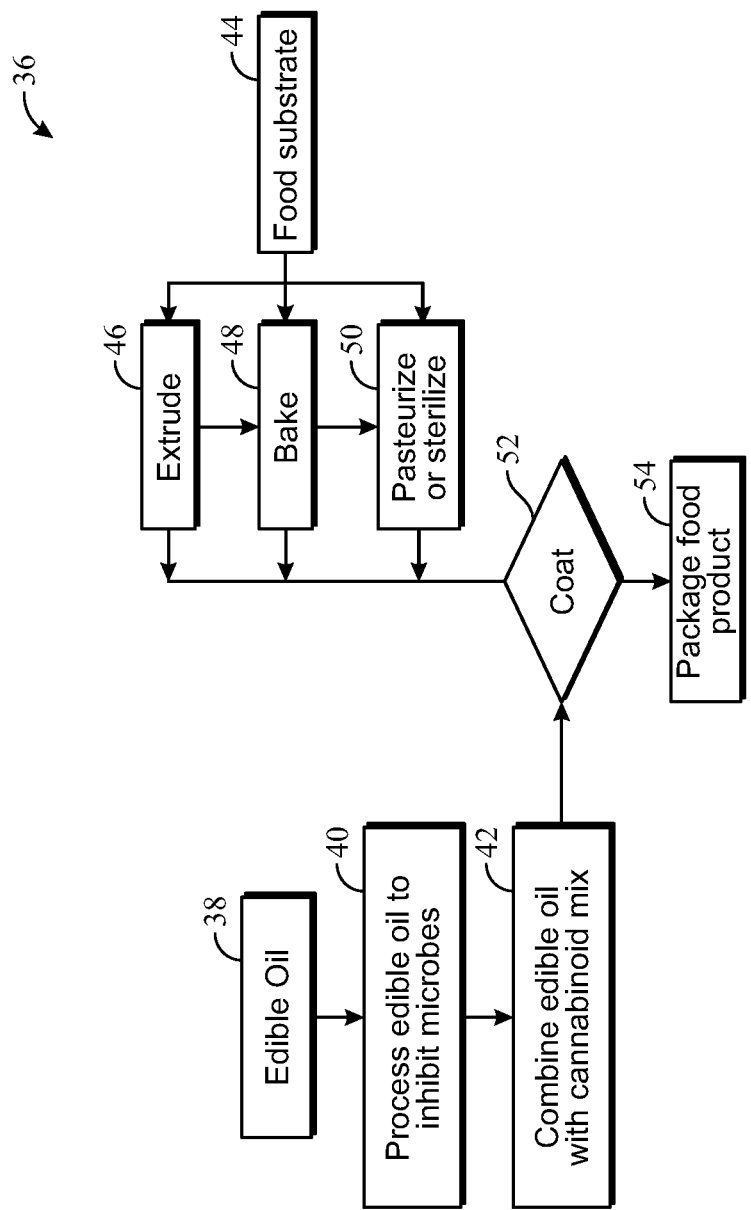
FIG. 2 is method of producing a packaged food product having classical cannabinoids in their acid form.

FIG. 2 shows a flow chart of a method in accordance with the present invention, generally designated with the reference numeral 36. The method 36 includes the step 38 of providing an edible oil, the step 40 of processing the edible oil to inhibit microbes and the step 42 of combining the edible oil with at least one cannabinoid and preferably a mix of cannabinoids. A mix of cannabinoids is termed "cannabinoid mix", which includes at least one cannabinoid such as CBD or THC-A, and other cannabinoids.

The step 40 of processing the edible oil to inhibit microbes can be accomplished by irradiation, heating, pressure treatment or other methods commonly used to treat edible oils. The step of processing increases shelf life and reduces health risks associated with pathogens.

The step 42 combines the processed edible oil with a cannabinoid mixture. In one embodiment the cannabinoids mix is preprocessed to inhibit microbes without significant decarboxylation of cannabinoids contained therein. Ideally no cannabinoids are decarboxylated. In another embodiment the ratio of non-decarboxylated cannabinoids to decarboxylated cannabinoids is at least 9:1.

In yet another embodiment the step of combining 42 precedes the step of processing 40 while maintaining a consistent ratio of non-decarboxylated cannabinoids to decarboxylated cannabinoids. In another embodiment the ratio of non-decarboxylated cannabinoids to decarboxylated cannabinoids is at least 9:1.

The method 36 includes the step 44 of providing a food substrate. The food substrate can be processed in any of a number of ways in order to obtain desired forms. These ways include the step 46 of extruding the food substrate in a hot or cold extrusion process, the step 48 of baking the food substrate, or the step 50 of pasteurizing or sterilizing the food substrate. In addition to these steps, other steps including dehydrating or otherwise cooking the food substrate can be implemented. The steps can be undertaken individually or combined in various ways to achieve food product. After the food substrate is processed, the step 52 coats the food substrate with the edible oil including the cannabinoids mix. The step of coating includes spraying according to one embodiment of the invention. In another embodiment of the invention the food substrate is soaked with the cannabinoid mix. The cannabinoid mix infuses and penetrates the food substrate to create a uniform distribution of cannabinoids in the food substrate. In another embodiment the step of coating 52 includes mixing to assure a uniform concentration of cannabinoids on the food substrate. Coating oils may subsequently penetrate/permeate the food substrate. In another embodiment, the food substrate and edible oil are subjected to a vacuum, wherein the edible oil penetrates and fills voids within the food substrate. The step 54 packages the infused food substrate as a packaged food product.

In one embodiment, the cannabinoid mix includes is hemp oil, such as hemp seed oil, or hemp oil derived from other parts of the hemp plant. The hemp oil is cold-pressed or extracted oil from industrial hemp. Preferably, the hemp oil is processed at 50° C. or lower and applied to the food substrate at 80° C. or lower. In a preferred embodiment of the invention, the hemp oil has no more than 10 ppm (0.001% by dry weight) tetrahydrocannabinol (THC).

In one embodiment the hemp seed is dehulled prior to being cold-pressed to limit psychoactive cannabinoid content, which is concentrated in the hull of the hemp seed.

In another embodiment, the hemp seed is ground prior to being cold-pressed so that cannabinoids in the hull and the endosperm are passed into the hemp oil to increase cannabinoid content of the hemp oil.

While hemp oil is used in various embodiments of the invention, it can be appreciated that the hemp oil can be supplemented by oils derived from other parts of the hemp plant, such as hemp stalk oil, hemp leaf oil, or hemp flower oil. Additionally, fractions derived from hemp oil can be added to the hemp oil. These include cannabinoids, bioactive terpenes, and essential fatty acids. Canine breeds and other mammals are unable to produce some particular essential fatty acids. In one embodiment, the hemp oil includes 60-80% (w/w) linoleic acid and alpha-linoleic acid. More preferably, the hemp oil includes 70-76% (w/w) linoleic acid and alpha-linoleic acid. Other beneficial ratios are possible.

In accordance with the present invention, the cannabinoids and the essential fatty acids of the hemp oil (omega-6 and omega-3 fatty acids) are protected from oxidation in at least one of a number of ways. In one embodiment, an anti-oxidant, or blends of anti-oxidants, are added to the hemp oil. In another embodiment, the hemp oil is blended with another oil to inhibit oxidation.

Preferably, the food product of the present invention includes a maximum oil content of 10% of combined oils by weight. More preferably, the food product of the present invention includes an oil content of with the range of 5% to 10% of combined oils by weight. In another embodiment the oil content is 4-8% of combined oils by weight. In another embodiment the oil content is less than 5% of combined oils by weight.

In one embodiment, the inventive food product includes hemp oil. The hemp oil content of the food product is between 4-8% by weight. In a variation of this embodiment, the hemp oil is blended with a second oil to inhibit oxidation of the acid-form cannabinoids in the hemp oil. The hemp oil includes active cannabinoids in micro-dose concentrations measured in parts per million. Preservation of these cannabinoids it is important to enable the cannabinoids to be bioactive. The blended oil preserves these cannabinoids and inhibits cannabinoid oxidation. The oil content of both the hemp oil and the blended oil remains below 10% of the product by weight.

The processing methods of the present invention reduce the oxidation of the essential fatty acids as well as the cannabinoids. Thus, the health benefits of the inclusion hemp oil are unencumbered.

Hemp oil samples were tested and contain measurable amounts of CBD and CBD-A, but no measurable THC at a level of quantification (LOQ) of 2.0 ppm. Preferably the CBD-A content averages between 15-35 ppm. In one embodiment, the CBD and CBD-A content of the hemp oil averages between 1050 ppm, and preferably between 10-40 ppm. Table 2 shows tested samples of hemp oil and indicates various cannabinoid concentrations in parts per million (ppm). Unopened samples direct from supplier stored in cool dark place (all values in PPM).

TABLE 2

| Lot Number | Organic | THC | Δ8-THC | Δ9-THC | THCA | THCV | CBC | CBD | CBDA | Totals |
|---|---|---|---|---|---|---|---|---|---|---|
| ANBE65NCA | N | 0.00 | 0.00 | 0.00 | 0.00 | 0.00 | 0.00 | 5.10 | 18.80 | 23.90 |
| GEWI15SCA | N | 0.00 | 0.00 | 0.00 | 0.00 | 0.00 | 0.00 | 10.10 | 20.10 | 30.20 |
| DAMA15XCA | N | 0.00 | 0.00 | 0.00 | 0.00 | 0.00 | 0.00 | 10.70 | 26.90 | 37.60 |
| BRSK36NOA | Y | 0.00 | 0.00 | 0.00 | 0.00 | 0.00 | 0.00 | 3.50 | 23.60 | 27.10 |
| ASBA16SOA | Y | 0.00 | 0.00 | 0.00 | 0.00 | 0.00 | 0.00 | 9.90 | 29.70 | 39.60 |
| Avg cannabinoids: | | 0.00 | 0.00 | 0.00 | 0.00 | 0.00 | 0.00 | 7.86 | 23.82 | 31.68 |

In another embodiment, the hemp oil is sprayed under vacuum pressure to improve absorption of the oil into the food product and to achieve a desired uniformity of concentration of the hemp oil in the food product. In another embodiment a clay is added to the food product to improve absorption of the oil into the food product. In another embodiment, the hemp oil is applied to the food product at a temperature greater than room temperature and less than the decarboxylation temperature of CBD-A.

Spray coating systems or drum coating systems can be used to apply the oil to the food product. In embodiments where the hemp oil is blended with other oils, animal fat oil can be used, or a vegetable derived oil such as coconut oil, or sunflower oil. Maximum total oil amount is 10%.

Optimally the hemp oil includes 74% (w/w) linolenic acid and alpha-linolenic acid. These fatty acids function as a bioactive excipient that optimally delivers the cannabinoids in vivo.

Essential Fatty Acids. Linolenic acid (an omega-6 FA) and alpha-linolenic acid (an omega-3 FA) have been measured by investigators as 52-62% and 12-23% (w/w) respectively in hemp oil. In a preferred embodiment the hemp oil is chosen to have approximately 54% omega-6 fatty acids linoleic and gamma linolenic and 18% omega-3 fatty acids alpha linolenic acid and stearidonic acid. This typically yields an approximate 3:1 ratio of omega-6 to omega-3. This ratio nears the 5:1 ratio of omega-6 to omega-3 fatty acids recommended for canine diets is achieved through supplementing with than other plant or meat sourced oils.

Many commercial pet foods in fact contain excess omega-6 which is known to be pro-inflammatory. In addition, hemp oil has phytosterols which can help reduce arterial inflammation. Further, hemp oil is a natural source of several minerals needed for homeostasis, including phosphorous, potassium, magnesium, sulfur, calcium, iron, and zinc. Thus, the present invention balances the ratio of omega-6/omega-3 fatty acids while supplementing phytosterols and minerals such as phosphorous, potassium, magnesium, sulfur, calcium, iron, and zinc. This, in combination with active cannabinoids, functions to reduce inflammation and achieve homeostasis.

FOOD INGREDIENTS, METHODS AND PRODUCTS

Example 1: Canine Feeding Method

The Resting Energy Requirement (RER) for an intact adult dog can be calculated by the formula RER=$1.8*70(BW)^{0.35}$ (SACN, p. 61). For a 20-kg dog, this calculation returns a daily caloric requirement of 1162 kcal per day. For a diet containing 3500 kcal/kg, this dog would optimally consume 1162 kcal/day±3500 kcal/kg=0.332 kg/day, or 332 grams of diet per day. If hemp oil is 2% of the diet, the dog would consume 6.64 grams of hemp oil per day, slightly more than one teaspoonful. One study (Holler, 2008) tested 29 hemp-containing samples of which 7 were oils; the highest concentration of THC found was 7.8 μg/g, or 0.00078%. Using this number, the 20-kg dog in the example above consuming 6.64 grams of oil would receive 0.052 mg of THC, or 0.003 mg/kg/day. Studies in humans, either after single or repeated exposure, identified psychotropic effects as a follow up of a single administration at the same lowest effective dose (the lowest dose tested) of 0.04 mg THC/kg BW, which is deemed to be a realistic approximation of the Lowest Observed Effect Level (LOEL) by the European Food Safety Authority (EFSA, 2011). This proposed use of hemp oil, even if cross-contaminated with THC, is far below the psychotropic LOEL. If greater amounts of hemp oil were anticipated in canine diets, a 20-kg dog fed 332 grams of diet consisting of 5% hemp oil would consume 16.6 grams of oil, or roughly one tablespoonful. Using the scenario above of 7.8 μg/g THC in the oil, this dog would consume 0.13 mg of THC per day, or 0.007 mg THC/kg/day, again well below any psychotropic effect. Accordingly, a method of the present invention includes delivering less than 0.13 mg of THC per day, or 0.007 mg THC/kg/day to a canine subject. Another method of the present invention is providing canine feed to a subject containing 0.02% cold pressed hemp oil, where the feed is manufactured at temperatures which neither oxidize the essential fatty acids in the hemp oil, nor oxidize the bioactive cannabinoids. Optionally, anti-oxidants can be added to the hemp oil to minimize oxidation of fatty acids.

Example 2: Sample Canine Food Formulation

| Ingredient: | % |
| --- | --- |
| Chicken meal | 0.372 |
| Brown rice | 0.19575 |
| Oats | 0.090 |
| Barley | 0.090 |
| Dried egg | 0.08 |
| Beet pulp | 0.04 |
| Brewers yeast | 0.035 |
| Chicken fat | 0.035 |
| Palatant | 0.035 |
| Hemp oil | 0.02 |
| Salmon Oil | 0.0055 |
| Vitamin/mineral | 0.00175 |
| Total | 1.000 |

Example 3: Sample Canine Food Formulation

| Ingredient: | % |
| --- | --- |
| Chicken meal | 0.37 |
| Sweet potato | 0.18075 |
| ground peas | 0.12 |
| Chickpeas | 0.12 |
| Dried egg | 0.08 |
| Chicken fat | 0.032 |
| Palatant | 0.035 |
| Brewers yeast | 0.035 |
| Hemp oil | 0.02 |
| Salmon Oil | 0.0055 |
| Vitamin/mineral | 0.00175 |
| Total | 1.000 |

Example 4 Nut Butter (Human Food)

Nut Butters: Edible oils for human consumption, such as hemp oil including cannabinoids, is mixed with nut butter created by blanching and grinding nuts. The edible oils including cannabinoids have minimal water content and would not normally be acidified so that the cannabinoids do not decarboxylate to a significant degree. In one embodiment, the nut butter is pressure treated before pack-out. In another embodiment, the edible oil is irradiated, filtered and/or pressure treated prior to mixing with the blanched and ground nuts. The cannabinoids have a ratio of acidic to non-acidic forms of the cannabinoids of at least 9:1. In one embodiment, the nut butter contains no detectable THC and only CBD-A. In another embodiment the nut butter contains no detectable THC and a combination of cannabinoids described herein including predominately CBD-A. Preferably, the edible oils and the blanched and dried nuts are simultaneously treated by irradiation, filtering, pressure treatment, or combinations thereof to improve shelf life and to inhibit microbial contamination.

Example 5 Spreads (Human Food)

A spread product includes acidic cannabinoids. Acidic cannabinoids are dissolved in an edible oil, which is mixed at a temperature of less than 80° C. into a spread product. Oils would have minimal water content and would not be acidified so that the acidic cannabinoids do not significantly decarboxylate. Optionally, the product could be pressure treated before pack-out. Optionally, the edible oil is processed to inhibit microbial growth through irradiation, filtering, pressure treatment, or combinations thereof prior to mixing with the spread product. This processing inhibits food-borne illness in consumers and improves shelf life of the spread product.

Example 6 Pourable Dressing (Human Food)

A pourable dressing product includes acidic cannabinoids. Acidic-cannabinoids are dissolved in an edible oil, or presented in the form of hemp oil, which is mixed at a temperature of less than 80° C. into a pourable dressing base. The edible oils have minimal water content and would not be acidified so that the acidic-cannabinoids do not significantly decarboxylate. Optionally, the product could be pressure treated before pack-out. Optionally, the edible oils are processed to inhibit microbial growth through irradiation, filtering, pressure treatment, or combinations thereof prior to mixing with the spread product. This processing inhibits food-borne illness in consumers and improves shelf life of the spread product. Desired combinations of the edible oils and cannabinoids are added, in whole, or in part, to the edible oil in the pourable dressing base.

The pourable dressing has minimal water content and would not be acidified to inhibit decarboxylation of the acidic-cannabinoids. The pourable dressing is pressure treated before pack-out. The edible oil is processed by irradiation, filtering, pressure treatment or combinations thereof prior to addition to the pourable dressing base.

Example 7 Chewing Gum (Human Food)

Edible oils such as hemp oil, that includes a cannabinoid mixture, are added to chewing gum. Optionally, the edible oil could be irradiated, filtered and/or pressure treated prior to addition to the chewing gum.

Example 8 Frozen Dairy Products (Human Food)

Combinations of edible oils and cannabinoids would be added, in whole, or in part, to the oil in the product. Oils would have minimal water content and would not be acidified. Optionally, the product could be pressure treated before pack-out. The oil could be irradiated, filtered and/or pressure treated prior to addition.

Example 9 Confections (Human Food)

A variety of confections can be produced at relatively high temperatures since ordinary sugar has a melting point of about 160° C. Artificial sweeteners, like aspartame (melting point is 248-250° C.), can have higher or lower melting points, which allows for processing at high temperatures. The process of producing confections with or without the heat and pressure combinations in extrusion can alter the cannabinoids and convert acidic forms to non-acidic forms. Cannabinoids can be added with or without other additives, flavorings, or ingredients by contact (drip, spray, bath, etc.) or other forms after the confection is formed or extruded and then cooled to less than 80° C. or lower.

Example 10 Extruded Pet Food

Pet food manufactured by extruding a pet food substrate where an edible oil including cannabinoids is added after drying and while the temperature of the pet food is less than 80° C. Optionally the pet food includes hemp oil as the edible oil. In a further option, the edible oil is infused with extracted or concentrated oil derived from the flowers or leaves of *Cannabis sativa*. Other oils can deliver the same benefits. If not then please delete sections that describe the benefits of hemp oil.

The combination of desired edible oils and the cannabinoids may improve the health of pets including canines, felines and other mammals.

Example 11 Livestock Feed

The present invention includes livestock rations manufactured by pelletizing where an edible oil including cannabinoids is added to the mix prior to pelletizing and while maintaining the processing temperature at less than 80° C. Alternatively, an edible oil including cannabinoids is applied/coated onto formed pellets.

Example 12 Poultry Feed

Feed manufactured by pelletizing where an edible oil including cannabinoids is added to the mix prior to pelletizing and while maintaining the processing temperature at less than 80° C. Alternatively, an edible oil including cannabinoids is applied/coated onto formed pellets.

Example 13 Small Animals

The present invention can be utilized for animals including birds, rodents, fish, herbivorous reptiles and insects. Feeds manufactured by pelletizing where an edible oil including cannabinoids is added to the mix prior to pelletizing and while maintaining the processing temperature at less than 80° C. Alternatively, an edible oil including cannabinoids is applied/coated onto formed pellets.

Example 14 Molded Pet Treats

Injection Molded Foods: target animals include dogs, cats, rodents and birds. Foods manufactured by injection molding where an edible oil including cannabinoids is added to the mix prior to molding and while maintaining the processing temperature at less than 80° C. Alternatively, an edible oil including cannabinoids is applied/coated onto molded products. In a further example, the molded product may be a treat rather than nutritionally complete food.

Example 15 Sausage (Human Food)

Dry Cured Sausage: a variety of sausages can be made by adding salt and nitrite/nitrate to meats and drying the mixtures at refrigeration temperatures. After sufficient moisture is removed then the mixtures can be further dehydrated at warmer temperatures. An edible oil including cannabinoids is added to the mix prior to drying. Optionally the meat mixtures can be smoked during dehydration. Optionally, an edible oil including cannabinoids is applied/coated onto sausages.

Although this invention pertains primarily to integration of cannabinoids into processed food products without significant molecular modification, the products and processes of the present invention can utilize any combination of cannabinoids, including combinations of the following cannabinoids: $\Delta$-9-tetrahydrocannibolic acid (THC-A), $\Delta$-9-tetrahydrocannibolic acid (THC-B), $\Delta$-9-tetrahydrocannibolic acid-$C_4$ A and/or B (THC-A-$C_4$), $\Delta$-9-tetrahydrocannibivarinic acid (THCVA), $\Delta$-9-tetrahydrocannibiorcolic acid A and/or B (THC-A-$C_1$), $\Delta$-8-tetrahydrocannibolic acid ($\Delta^8$-THC-A), cannabicyclolic acid (CBL-A), cannabidiolicacid (CBD-A), cannabigerolic acid (CBG-A), cannabigerovarinic acid (CBGV-A), cannabichromenic acid (CBCA), cannabichromevarinic acid (CBCVA), cannabidivarinic acid (CBDVA), cannabielsoic acid A (CBEA-A), cannabielsoic acid B (CBEA-B), cannabielsoic C3 acid B (CBEA-$C_3$ B) and cannabinolic acid (CBNA). Appendix A of the present patent application shows various selected cannabinoids including chemical formulations and properties.

While the present invention is described in terms of various embodiments of the invention and examples thereof, the scope of the present invention is defined in the appended claims. Further it can be appreciated that the concentrations of edible oils, particularly hemp oil, can be utilized in all of the mentioned food products. Also, the micro-dosing, preservation, and concentration of cannabinoids including cannabidiolic acid can be utilized in all of the mentioned food products as well as other food products. The present invention can be used for a variety of pet foods including feline, canine, and others. Further, the present invention can be used for livestock feed, as well as for human food.

What is claimed is:

1. A nutritionally complete animal food including, vitamins, and minerals to sustain the animal's health and wellness;
   one or more ingredients containing cannabinoids added to the nutritionally complete animal food at the time of manufacturing;
   the cannabinoids are selected from the group consisting of Cannabichromenic acid (CBCA), Cannabidiolic acid (CBDA), Cannabidivarinic acid (CBDVA), Cannabigerolic acid (CBGA), Cannabinolic acid (CBNA), $\Delta$9-Tetrahydrocannabinolic acid (THCA), Tetrahydrocannabinolic acid (THCVA) and combinations thereof,
   and the concentrations of each of the cannabinoids are each less than 100 parts per million (ppm) in the at least one ingredient.

2. The nutritionally complete animal food as set forth in claim 1, wherein the one or more ingredient containing cannabinoids further includes decarboxylated cannabinoids selected from the group consisting of Cannabichromene (CBC), Cannabidiol (CBD), Cannabidivarin (CBDV), Cannabigerol (CBG), Cannabinol (CBN), $\Delta$9-Tetrahydrocannabinol (THC), Tetrahydrocannabivarin (THCV), and combinations thereof.

3. The nutritionally complete animal food as set forth in claim 2, wherein the at least one ingredient further comprises $\Delta$9-Tetrahydrocannabinolic acid (THCA) in a concentration of less than 100 parts per million (ppm) in each of the at least one ingredients.

4. The nutritionally complete animal food as set forth in claim 2, wherein the at least one ingredient further comprises Cannabidiol (CBD) in a concentration of less than 100 parts per million (ppm) in each of the at least one ingredients.

5. The nutritionally complete animal food set forth in claim 2, wherein the food product is formulated to limit the daily intake of any individual cannabinoid in the group to a maximum of 1.5 parts per million (ppm) per kilogram (kg) of body weight per 24 hr. day (1.5 ppm/kg BW/day) under normal and repeated feeding conditions to sustain the animal's health and wellness.

6. The nutritionally complete animal food set forth in claim 1, wherein the food product is formulated to limit the daily intake of any individual cannabinoid in the group to a maximum of 1.5 parts per million (ppm) per kilogram (kg) of body weight per 24 hr. day (1.5 ppm/kg BW/day) under normal and repeated feeding conditions to sustain the animal's health and wellness.

7. A complete animal feed product formulated with at least one ingredient containing cannabinoids;
the at least one ingredient containing cannabinoids includes Cannabidiolic acid (CBDA) and Cannabichromenic acid (CBCA) in a ratio of at least 1:3, and
the combined concentration of Cannabidiolic acid (CBDA) and Cannabichromenic acid (CBCA) is less than 100 parts per million (ppm) in the at least one ingredient.

8. A nutritionally complete animal feed product formulated with at least one ingredient containing cannabinoids;
the at least one ingredient containing cannabinoids includes Cannabidiolic acid (CBDA) and Cannabichromene (CBC) in a ratio of at least 1:3, and
the combined concentration of Cannabidiolic acid (CBDA) and Cannabichromene (CBC) is less than 100 parts per million (ppm) in the at least one ingredient.

9. A nutritionally complete animal feed product formulated with at least one ingredient containing cannabinoids;
the at least one ingredient containing cannabinoids includes Cannabidiolic acid (CBDA) and Cannabidiol (CBD) in a ratio of at least 1:20,
and the combined concentration of Cannabidiolic acid (CBDA) and Cannabidiol (CBD) is less than 100 parts per million (ppm) in the at least one ingredient.

10. A nutritionally complete animal feed product formulated with at least one ingredient containing cannabinoids;
the at least one ingredient containing cannabinoids includes Cannabidiolic acid (CBDA) and Cannabidivarinic acid (CBDVA) in a ratio of at least 1:3,
and the combined concentration of Cannabidiolic acid (CBDA) and Cannabidivarinic acid (CBDVA) is less than 100 parts per million (ppm) in the at least one ingredient.

11. A nutritionally complete animal feed product formulated with at least one ingredient containing cannabinoids;
the at least one ingredient containing cannabinoids includes Cannabidiolic acid (CBDA) and Cannabidivarin (CBDV) in a ratio of at least 1:3, and
the combined concentration of Cannabidiolic acid (CBDA) and Cannabidivarin (CBDV) is less than 100 parts per million (ppm) in the at least one ingredient.

12. A nutritionally complete animal feed product formulated with at least one ingredient containing cannabinoids;
the at least one ingredient containing cannabinoids includes Cannabidiolic acid (CBDA) and Cannabigerolic acid (CBGA) in a ratio of at least 1:3,
and the combined concentration of Cannabidiolic acid (CBDA) and Cannabigerolic acid (CBGA) is less than 100 parts per million (ppm) in the at least one ingredient.

13. A nutritionally complete animal feed product formulated with at least one ingredient containing cannabinoids;
the at least one ingredient containing cannabinoids includes Cannabidiolic acid (CBDA) and Cannabigerol (CBG) in a ratio of at least 1:3,
and the combined concentration of Cannabidiolic acid (CBDA) and Cannabigerol (CBG) is less than 100 parts per million (ppm) in the at least one ingredient.

14. A nutritionally complete animal feed product formulated with at least one ingredient containing cannabinoids;
the at least one ingredient containing cannabinoids includes Cannabidiolic acid (CBDA) and Cannabicyclol (CBL) in a ratio of at least 1:3, and
the combined concentration of Cannabidiolic acid (CBDA) and Cannabicyclol (CBL) is less than 100 parts per million (ppm) in the at least one ingredient.

15. A nutritionally complete animal feed product formulated with at least one ingredient containing cannabinoids;
the at least one ingredient containing cannabinoids includes Cannabidiolic acid (CBDA) and Cannabinolic acid (CBNA) in a ratio of at least 1:3, and
the combined concentration of Cannabidiolic acid (CBDA) and Cannabinolic acid (CBNA) is less than 100 parts per million (ppm) in the at least one ingredient.

16. A nutritionally complete animal feeding product formulated with at least one ingredient containing cannabinoids;
the at least one ingredient containing cannabinoids includes Cannabidiolic acid (CBDA) and Cannabinol (CBN) in a ratio of at least 1:3, and
the combined concentration of Cannabidiolic acid (CBDA) and Cannabinol (CBN) is less than 100 parts per million (ppm) in the at least one ingredient.

17. A nutritionally complete animal feeding product formulated with at least one ingredient containing cannabinoids;
the at least one ingredient containing cannabinoids includes Cannabidiolic acid (CBDA) and Δ9-Tetrahydrocannabivarinic acid (THCA) in a ratio of at least 1:3,
and the combined concentration of Cannabidiolic acid (CBDA) and Δ9-tetrahydrocannabinolic acid (THCA) is less than 100 parts per million (ppm) in the at least one ingredient.

18. A nutritionally complete animal food product formulated with at least one ingredient containing cannabinoids;
the at least one ingredient containing cannabinoids includes Cannabidiolic acid (CBDA) and Δ9-Tetrahydrocannabinol (THC) in a ratio of at least 1:3, and
the combined concentration of Cannabidiolic acid (CBDA) and Δ9-Tetrahydrocannabinol (THC) are less than 100 parts per million (ppm) in the at least one ingredient.

19. A nutritionally complete animal feeding product formulated with at least one ingredient containing cannabinoids;
the at least one ingredient containing cannabinoids includes Cannabidiolic acid (CBDA) and Tetrahydrocannabivarinic acid (THCVA) in a ratio of at least 1:3, and
the combined concentrations of Cannabidiolic acid (CBDA) and Δ9-tetrahydrocannabinolic acid (THCVA) is less than 100 parts per million (ppm) in the at least one ingredient.

20. A nutritionally complete animal feeding product formulated with at least one ingredient containing cannabinoids;
the at least one ingredient includes Cannabidiolic acid (CBDA) and Tetrahydrocannabivarin (THCV) in a ratio of at least 1:3, and
the combined concentration of Cannabidiolic acid (CBDA) and Tetrahydrocannabivarin (THCV) is less than 100 parts per million (ppm) in the at least one ingredient.

\* \* \* \* \*